US006332865B1

United States Patent
Borody et al.

(10) Patent No.: US 6,332,865 B1
(45) Date of Patent: Dec. 25, 2001

(54) SELF-ADVANCING ENDOSCOPE

(76) Inventors: Thomas Julius Borody, 144 Great North Road, Five Dock, New South Wales, 2046; Peter Stephenson, Level 2, 35 Astor Terrace, Brisbane, Queensland 4000; John Begg; Peter Ayre, both of 126 Greville Street, Chatswood, New South Wales 2067, all of (AU)

( * ) Notice: Subject to any disclaimer, the term of this patent is extended or adjusted under 35 U.S.C. 154(b) by 0 days.

(21) Appl. No.: 09/582,853
(22) PCT Filed: Jan. 7, 1999
(86) PCT No.: PCT/AU99/00005
  § 371 Date: Aug. 14, 2000
  § 102(e) Date: Aug. 14, 2000
(87) PCT Pub. No.: WO99/34726
  PCT Pub. Date: Jul. 15, 1999

(30) Foreign Application Priority Data
Jan. 7, 1998 (AU) .................................... PP1236

(51) Int. Cl.⁷ ..................................... A61B 1/01
(52) U.S. Cl. ..................... 600/114; 604/95.01; 356/241.1
(58) Field of Search .................. 600/114; 604/95.01; 356/241.1

(56) References Cited

U.S. PATENT DOCUMENTS

| 5,345,925 | 9/1994 | Allred, III et al. | 128/4 |
| 5,562,601 | 10/1996 | Takada | 600/114 |
| 5,662,587 | * 9/1997 | Grundfest et al. | 600/114 |

FOREIGN PATENT DOCUMENTS 9600517    1/1996   (WO).

OTHER PUBLICATIONS

Patent Abstracts of Japan of JP08089476A and drawings therefor of Apr. 1996.
Patent Abstracts of Japan of JP07116112A and drawings therefor of May 1995.

* cited by examiner

*Primary Examiner*—John Mulcahy
(74) *Attorney, Agent, or Firm*—Ladas & Parry

(57) ABSTRACT

A self-advancing endoscope (10) comprising an elongated flexible tubular member (12) and an elongated channel (14) defined by the tubular member (12) and having a distal end wall (16). Piston means (22) are slideably disposed in the channel (14) toward the distal end wall (16). The endoscope (10) also comprises means (24, 26) for reciprocating the piston means (22) such that the piston means (22) impacts the distal end wall (16) on an advancing stroke.

15 Claims, 1 Drawing Sheet

SELF-ADVANCING ENDOSCOPE

FIELD OF THE INVENTION

This invention relates to a self-advancing endoscope.

BACKGROUND OF THE INVENTION

Endoscopes are long, tubular instruments used to examine endoluminally distant, confined spaces in humans, animals or in various types of equipment. Endoscopes are flexible, carry a powerful light which illuminates the passage to be examined from the tip of the endoscope, possess either fibreoptic or video image acquisition ports, and contain a series of channels running throughout their length to allow air insufflation, water injection and insertion of tubular instruments, such as forceps, snares, needles or retrieval forceps among others.

Insertion of endoscopes, or similar devices such as boroscopes, gastroscopes, colonoscopes or enteroscopes, as used in examination of narrow passages, whether it be within human or animal bodies or in narrow spaces within machinery is relatively simple over short distances but progressively more difficult with increasing distance of insertion. For example, gastroscopy in humans is easily achieved by using a relatively stiff endoscope with a flexible end which can rapidly reach the second part of the duodenum. However, to continue introducing such an instrument beyond the duodenum becomes increasingly difficult because, despite the relative stiffness of the instrument, it loops within the stomach as it is inserted more deeply.

Although enteroscopes have been developed to traverse the small bowel, stiffening tubes (known as overtubes) are needed to stiffen the instrument within the stomach so that looping will not occur.

Colonoscopes are readily passed through the rectum and left-side of the colon but difficulties can arise when one wants to routinely reach the caecum or terminal ileum.

In other words, there is an increasing difficulty in reaching more distal parts of the bowel in people or distal parts of a confined space when attempting to introduce any type of endoscope into a confined space. Further, in working with human endoscopes there is also the need for rapid insertion to minimise human suffering and to minimise the possibility of rupture.

Self-advancing endoscopes are disclosed in U.S. Pat. Nos. 4,934,786, 5,345,925 and 5,562,601. The devices disclosed in these patents all rely on the outer surface of the endoscope having a relatively movable portion that grips the internal wall of the passage through which the endoscope is passing. In this way, they do not only rely on external pushing as their source of forward (advancing) motion. However, the devices disclosed are all relatively complex in construction.

SUMMARY OF THE INVENTION

According to a first broad aspect of the invention there is provided a self-advancing endoscope comprising:

an elongated flexible tubular member;

an elongated channel defined by said tubular member and having a distal end wall;

piston means slideably disposed in said channel toward said distal end wall; and means for reciprocating said piston means such that said piston means impacts said distal end wall on an advancing stroke.

The piston means is typically be a solid piston.

The piston means is preferably reciprocated by mechanical means.

Preferably, the mechanical means for reciprocating said piston means comprises a reciprocating solenoid located at a proximal end of said channel and operatively coupled to said piston means.

The reciprocating solenoid may be coupled to said piston means by a flexible wire extending along said channel or, alternatively, by fluid sealed in said channel between said piston means and said solenoid.

In an alternate embodiment, the piston means is a column of fluid.

According to a second broad aspect of the invention there is provided a method of performing colonoscopy or enteroscopy in human or animals, said method comprising the step of using the self-advancing endoscope defined above,

BRIEF DESCRIPTION OF THE DRAWING

An embodiment of the invention will now be described, by way of example only, with reference to the accompanying drawing, in which.

DETAILED DESCRIPTION OF THE PREFERRED EMBODIMENT

Figure 1:
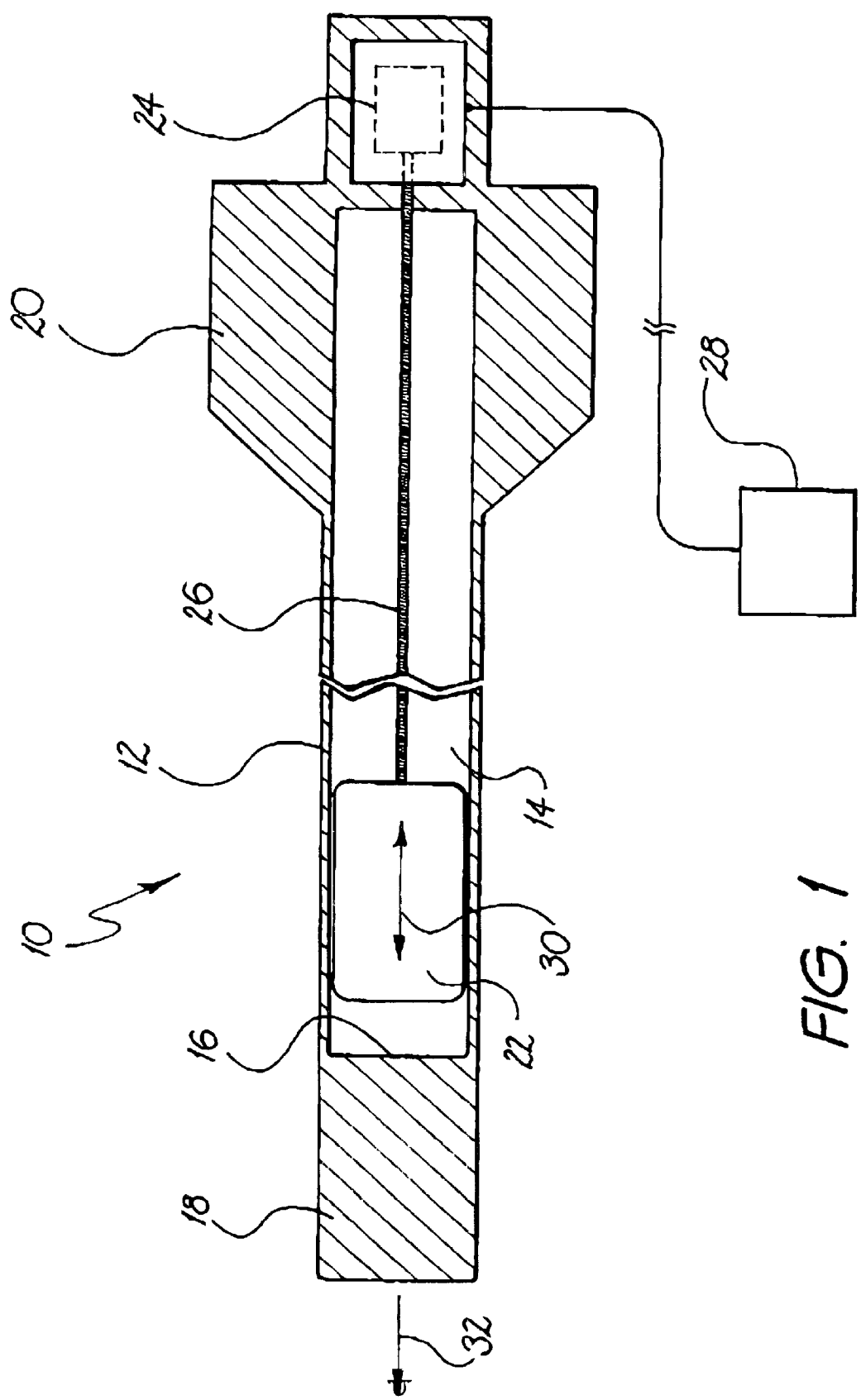
FIG. 1 is a cross-sectional schematic view of an embodiment of the invention

FIG. 1 shows an embodiment of a self advancing endoscope 10 according to the invention. The endoscope 10 comprises an elongated flexible tubular member 12, preferably produced from a plastics material, having an elongated channel 14 defined by the tubular member 10. The elongated channel 14 has a distal end wall 16. The end wall 16 is adjacent the distal tip or head 18 of the endoscope 10. The proximal end of the endoscope 10 includes an external gripping portion 20.

A piston means, in the form of steel piston 22, is slideably disposed in the channel 14 towards the end wall 16. A means for reciprocating the piston 22, in the form of a reciprocating solenoid 24, is mounted adjacent the gripping portion 20. The solenoid 24 is connected to the piston 22 by a flexible wire 26. The wire 26 is ideally narrow and flexible to allow it to bend in concert with the flexible member 12 of the endoscope 10 and to move rapidly with minimal resistance through the channel 14. Most preferably the wire 26 is similar in design to a piano wire with a flexible though solid wire core with an encircling tight wire casing running the length of the wire core and resembles the currently available endoscopic biopsy forceps wire.

A combined frequency generator and power source 28 is used to drive the solenoid 24 in a reciprocating fashion. The reciprocating motion of the solenoid 24 is transmitted to the piston 22 by the wire 26 causing the piston to also reciprocate, as indicated by double ended arrow 30.

The piston 22 is positioned in the channel 14 such that it impacts the distal end wall 16 on each advancing stroke (ie. each stroke to the left with reference to FIG. 1). The impact of the piston 22 against the end wall 16 transfers momentum from the piston 22 to the head 18 of the endoscope 10 thereby acting to advance the endoscope 10 in the direction indicated by arrow 32. The momentum of the piston 22 during its retracting stroke (ie. each stroke to the right with reference to FIG. 1) is absorbed by the user holding the gripping portion 20, which remains external the passage that the endoscope is inserted.

The present invention therefore provides a self-advancing endoscope 10 which requires no moving external parts to achieve propulsion.

In the embodiment shown, the tubular member 12 is approximately 1700 mm long. The piston 22 has an external diameter of 10 mm and a length of 25 mm. The internal diameter of the channel 14 is slightly larger than 10 mm to allow air to pass between the channel and the piston. Driving the piston through a stroke of 25 mm at a frequency of 30 Hertz has been found to be suitable for advancing the endoscope into a human patient.

The endoscope has a reliable, powerful propulsion unit which causes the endoscope to take small forward steps which overcome its external resistance. The endoscope possesses its propulsion unit (the piston) in its front and hence reduces loops previously described which are generated by pushing the instrument from its rear. This is of some importance in the field of colonoscopy as it protects the patient from loop-induced forceful colon rupture. In addition the front end "pull" of the endoscope greatly accelerates passage through the lumen being examined thus shortening the length of the procedure. Furthermore, in prevent looping during use, pain is minimised allowing rapid procedures to be carried out in a proportion of patients without the need for sedation or anaesthesia thus reducing costs, patient suffering and complications.

Apart from endoluminal uses of the advancing device in human gastrointestinal endoscopy, this endoscope is also useful in endoluminal examination in animals, such as in veterinary use. In other human and veterinary use the endoscope can be adapted and incorporated into instruments used in examining the lumina of veins, arteries, the biliary tree, urologic passages (urethra, bladder, ureters), in small bowel intubation, such as for motility studies, or deep intubation. The endoscope can also be built to be re-useable or with disposable catheters. Furthermore, to overcome intra-abdominal looping a per-laparoscopic instrument can carry the endoscope to allow entry into less accessible spaces including passage through the foramen of Winslow to examine the pancreas. Industrial applications would enable access of the endoscope into deeper and less accessible spaces enabling repairs and examinations without the need to dismantle, such as in the wings in aircraft.

Although the invention has been described with reference to a specific example, it will be appreciated by those skilled in the art that the invention may be embodied in many other forms.

For example, possible piston arrangements can include flexible metal rods (singly or in tandem), ball bearings, various heavy fluids within the channel eg water, oils, or mercury.

Further, an air vent can be provided in narrow versions of the piston 10. However, in the preferred embodiment, adequate venting of the air in the channel 14 is available via the space between the piston 22 and the interior of the channel 14 allows air to pass backwards as the piston 22 is driven forwards towards the end wall 16. The material of the flexible member 12 and the channel 14 ideally has a low coefficient of friction and is flexible. It may be constructed from metals or plastic. In its best example it is constructed from teflon or similar plastic. It may be used without or with lubrication, such as oils, silicon. or graphite among others.

Various other methods can also be used to propel the piston and wire or equivalent arrangement. These include pumps with a repeating cycle for fluid pistons (ie water, oils, mercury or compressed air), mechanical devices with a cam arrangement to repeatedly advance and withdraw the wire, or electromagnetic propulsion using a solenoid and a luminal ferromagnetic material in the piston and wire arrangement which constitutes the preferred embodiment of the invention shown in FIG. 1.

The electromagnetic propelling mechanism can be controlled with a footpedal (not shown) or other controller, for example, to adjust the speed and/or stroke of the piston movement and hence movement of the endoscope. If space is available within the cross-sectional diameter of the instrument, such as in colonoscopes, more than one such accelerating device could be fitted per endoscope to produce a smoother acceleration and, for example, to lower the distortion of picture acquisition.

What is claimed is:

1. A self-advancing endoscope comprising:

an elongated flexible tubular member;

an elongated channel defined by said tubular member and having a distal end wall; piston means slideably disposed in said channel toward said distal end wall; and means for reciprocating said piston means such that said piston means impacts said distal end wall on an advancing stroke.

2. The self-advancing endoscope of claim 1, wherein said piston means is a solid piston.

3. The self-advancing endoscope of claim 2, wherein the piston means is reciprocated by mechanical means.

4. The self-advancing endoscope of claim 1, wherein the piston means is reciprocated by mechanical means.

5. The self-advancing endoscope of claim 4 wherein said mechanical means for reciprocating said piston means comprises a reciprocating solenoid located at a proximal end of said channel and operatively coupled to said piston means.

6. The self-advancing endoscope of claim 5, wherein said reciprocating solenoid is operatively coupled to said piston means by a flexible wire extending along said channel.

7. The self-advancing endoscope of claim 5, wherein said reciprocating solenoid is operatively coupled to said piston means by fluid sealed in said channel between said piston means and said solenoid.

8. The self-advancing endoscope of claim 1 wherein said piston means is a column of fluid.

9. A method of performing colonoscopy or enteroscopy in humans or animals, said method including the step of using the self-advancing endoscope as defined in claims 1.

10. A method of performing colonoscopy or enteroscopy in humans or animals, said method including the step of using the self-advancing endoscope as defined in claim 2.

11. A method of performing colonoscopy or enteroscopy in humans or animals, said method including the step of using the self-advancing endoscope as defined in claim 4.

12. A method of performing colonoscopy or enteroscopy in humans or animals, said method including the step of using the self-advancing endoscope as defined in claim 5.

13. A method of performing colonoscopy or enteroscopy in humans or animals, said method including the step of using the self-advancing endoscope as defined in claim 6.

14. A method of performing colonoscopy or enteroscopy in humans or animals, said method including the step of using the self-advancing endoscope as defined in claim 7.

15. A method of performing colonoscopy or enteroscopy in humans or animals, said method including the step of using the self-advancing endoscope as defined in claim 8.

* * * * *